United States Patent [19]

Bailey

[11] Plant 4,833

[45] Mar. 30, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,661

[22] Filed: Sep. 9, 1980

[51] Int. Cl.[3] ..... A01H 5/00

[52] U.S. Cl. ..... Plt./20

[58] Field of Search ..... Plt./20

*Primary Examiner*—James R. Feyrer

*Attorney, Agent, or Firm*—Vincent G. Gioia

[57] ABSTRACT

A new hybrid tea rose variety of substantially nonfading bright red coloring.

1 Drawing Figure

1

The present invention relates to a new and distinct variety of rose plant of the hybrid tea rose class, which was originated by my crossing as seed parent the rose known as "Christian Dior" and the rose known as "Mr. Lincoln" as pollen parent.

Among the novel characteristics possessed by this new variety which distinguish it from its parents and all other varieties of which I am aware are brilliant red, substantially non-fading, non-bluing, singly borne blooms, developing from long buds and a vigorous, free branching plant with abundant foliage dense to ground level and outstanding disease resistance. Blooms are very long lasting on the plant and as cut flowers. Asexual reproduction by budding of the new variety as performed in Kern County, Calif., shows that the foregoing and other distinguishing characteristics come true to form and are established and transmitted through succeeding propagations.

The new and improved rose variety which I have developed is an unusually fine hybrid tea rose of strong red coloring which holds well and has outstanding substance displayed on a vigorous, free branching plant with abundant disease resistant foliage. The flowers are of heavy petalage but open well and have a good old rose fragrance.

The accompanying drawing shows typical specimens of the vegatative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "42B" is plate 42B of the Royal Horticultural Society Color Chart.

Parentage: Seedling.
*Seed parent.*—"Christian Dior".
*Pollen parent.*—"Mr. Lincoln".
Class: Hybrid tea.

The following observations are made of specimens grown outdoors in Kern County, Calif. during the month of November.

FLOWER

Blooming habit: Continuous.

A. Bud:

2

(1) *Size.*—Large.
(2) *Form.*—Long.
(3) *Color.*—When sepals first divide — near 42B. When petals begin to unfurl — near 42B.
(4) *Sepals.*—Long, fancy, well foliated, longer than bud.
(5) *Peduncle.*—Length — 3 to 4 inches. Aspect — straight. Strength — erect, strong. Color — near 138A.

B. Bloom:
(1) *Size.*—Average size when fully expanded — about 5 to 5½ inches.
(2) *Borne.*—Primarily singly, sometimes small clusters.
(3) *Form.*—High centered to cupped becoming flat, petals quill and recurve.
(4) *Petalage.*—Number of petals under normal conditions — about 38.
(5) *Color.*—Petal coloring both top and underside surfaces is generally 42B to 42A, newly unfurled petals have vibrant velvet texture adding to brilliance of the coloring. Color does not change greatly upon aging so that general tonality from a distance remains bright red.

C. Petals:
(1) *Texture.*—Very thick, good substance.
(2) *Appearance.*—Velvety.
(3) *Form.*—Rounded.
(4) *Arrangement.*—Regularly arranged.
(5) *Petaloids in center.*—Few.
(6) *Persistence.*—Drop off cleanly.
(7) *Fragrance.*—Good old rose fragrance.
(8) Lasting quality.—Very long lasting on plant and as cut flower.

REPRODUCTIVE ORGANS

A. Stamens, filaments and anthers:
(1) *Arrangement.*—Regularly arranged about styles.
(2) *Color.*—34C.

B. Pollen:
*Color.*—17C.

C. Styles: Medium length, strong.

D. Stigmas:
*Color.*—32C.

E. Hips:
*Shape.*—Globular.
*Size.*—Large, smooth.
*Color.*—28B.
*Do seeds protrude.*—No.

PLANT

A. Form: Upright.

B. Growth: Very vigorous, uniform branching, many canes break from bud union.

*Height attained.*—About 5 feet.

C. Foliage: Compound 5 to 7 leaflets.

(1) *Size.*—Large.

(2) *Quantity.*—Abundant, dense to ground level.

(3) *Color.*—New foliage: Upper side — near to 147A with purplish veining. Under side — near to 147C with purplish tonality. Old foliage: Upper side — near but darker than 137A. Under side — near 138B.

(4) *Shape.*—Oval.

(5) *Texture.*—Upper side is leathery and under side is dull.

(6) *Edge.*—Serrated.

(7) *Serration.*—Simple.

(8) *Leaf stem.*—Color — near to 137A but darker. Under side — near 138B.

(9) *Stipules.*—Long, slightly bearded.

(10) *Resistance to disease.*—Blackspot — excellent. Mildew — excellent. Rust — excellent.

D. Wood:

(1) *New wood.*—Color — near 137D with reddish cast. Bark — smooth.

(2) *Old wood.*—Color — near 138A on upper growth and 146A on lower parts of plant. Bark — smooth.

E. Thorns:

(1) *Thorns.*—Quantity (main stalk): few. On laterals from stalk — very few. Form — flat. Length — long. Color — near 146A to 137D. Position — regular.

(2) *Prickles.*—Few.

F. Winter hardiness: Good winter hardiness.

I claim:

1. A new and distinct variety of rose plant of the hybrid tea class, substantially as shown and described, characterized particularly by large brilliant red flowers which hold color well upon aging, are borne primarily singly to a stem and are long lasting on the plant and as cut flowers.

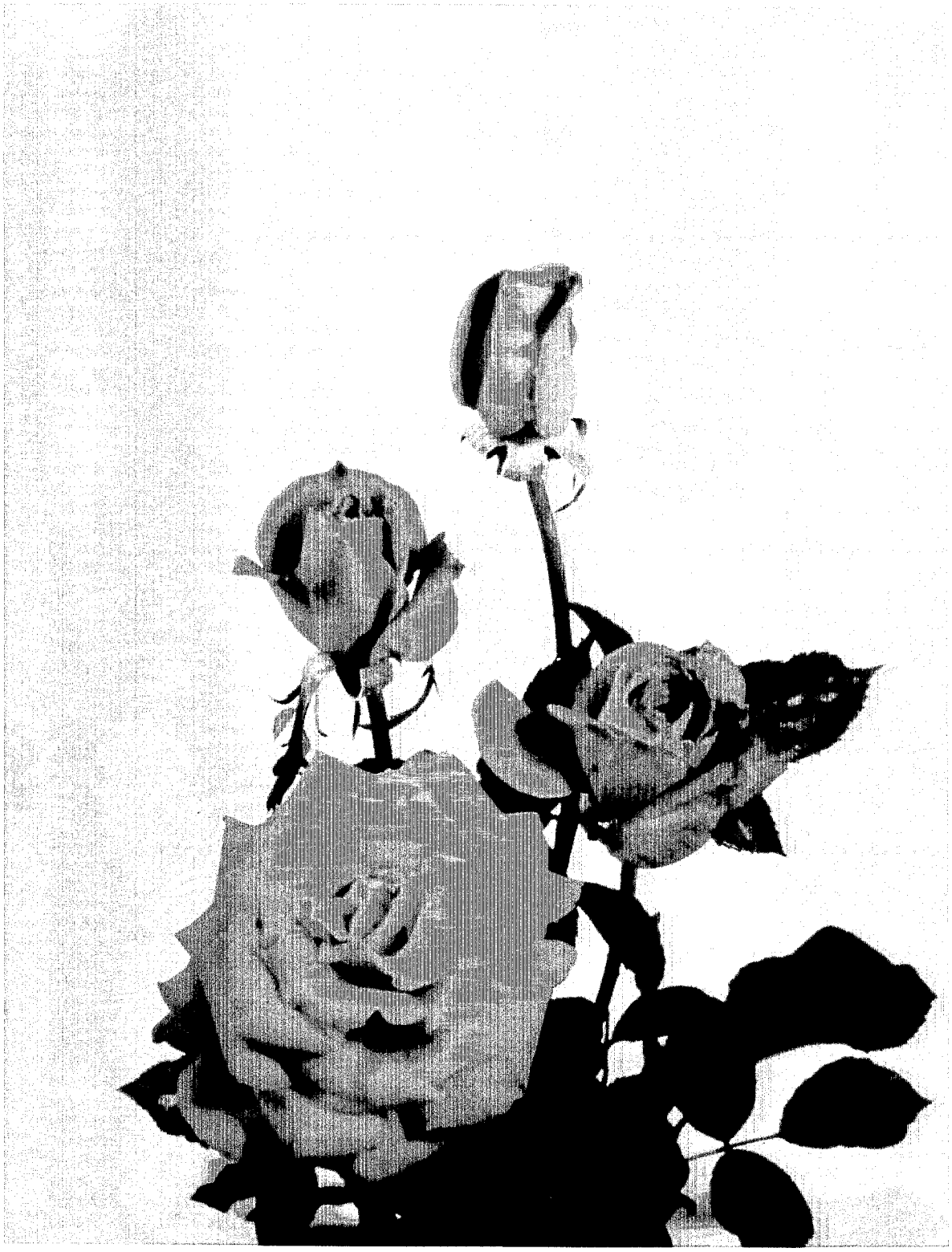

* * * * *